United States Patent [19]

Kerr et al.

[11] Patent Number: 5,001,141

[45] Date of Patent: Mar. 19, 1991

[54] N-(2-(2-OXO-1-IMIDAZOLIDINYL)ETHYL)-3-PHENYL-UREA AND ANALOGS AS AGENTS FOR INDUCTION OF ANTIOXIDANT ENZYMES

[75] Inventors: Janet S. Kerr; George A. Boswell, both of Wilmington, Del.

[73] Assignee: E. I. Du Pont de Nemours and Company, Wilmington, Del.

[21] Appl. No.: 389,896

[22] Filed: Aug. 4, 1989

Related U.S. Application Data

[63] Continuation-in-part of Ser. No. 211,314, Jun. 24, 1988, abandoned.

[51] Int. Cl.[5] ............................................ A61U 31/415
[52] U.S. Cl. ...................................... 514/398; 514/401
[58] Field of Search ................................. 514/398, 401

[56] References Cited

U.S. PATENT DOCUMENTS 4,032,638  1/1977  Wat ...................................... 514/269

Primary Examiner—Stanley J. Friedman

[57] ABSTRACT

N-[2-(2-oxo-1-imidazolidinyl)ethyl]-3-phenylurea and analogs are useful for protecting against oxygen-derived free radical damage in mammals, by inducing endogenous antioxidant enzymes, including superoxide dismutase, in mammals.

10 Claims, No Drawings

N-(2-(2-OXO-1-IMIDAZOLIDINYL)ETHYL)-3-PHENYL-UREA AND ANALOGS AS AGENTS FOR INDUCTION OF ANTIOXIDANT ENZYMES

CROSS-REFERENCE TO RELATED APPLICATION

This is a continuation-in-part of application No. 211,314 filed June 24, 1988.

BACKGROUND OF THE INVENTION

U.S. Pat. Nos. 3,859,301; 3,973,946; and 4,032,638, issued Jan. 7, 1975, Aug. 10, 1976, and June 28, 1977, respectively, to Wat describe substituted ureas useful in preventing ozone damage in plants.

Compounds described in the above U.S patents have now been found to induce antioxidant enzymes in mammals. These compounds may therefore be useful for the prevention and/or treatment of diseases mediated by oxygen derived free radicals, including cardiovascular, inflammatory, or central nervous system diseases.

SUMMARY OF THE INVENTION

According to the present invention, there is provided a method of protecting against oxygen-derived free radical damage in a mammal by inducing endogenous antioxidant enzymes, comprising administering to the mammal a protective amount of a compound of the formula:

$$Z-NH-CO-NH(CH_2)_n-N\underset{(CH_2)_{n'}}{\overset{\overset{L}{\|}}{\diagup}}Y \quad (I)$$

where
L=O or S;
Y=O or NH;
Z=naphthyl, or phenyl or substituted phenyl, optionally substituted with 1 or 2 groups selected from:
$C_1$-$C_6$ alkyl, straight or branched, $C_3$-$C_6$ cycloalkyl, $NO_2$, $S(O)_pR^1$, halogen, $N(O)_{n'}R^1R^2$, $OR^3$, $CF_3$.

$$-N\diagdown\diagup NH \quad \text{or} \quad -N\diagdown\diagup O,$$

or Z=

$$\underset{S}{\diagup\!\!\diagdown}, \quad \underset{O}{\diagup\!\!\diagdown} \quad \text{or} \quad \underset{\underset{R^1}{N}}{\diagup\!\!\diagdown};$$

n'=0 or 1;
n=0, 2 or 3;
p=0–2;
$R^1$ and $R^2$ are, independently, H, $C_1$-$C_6$ alkyl, and $R^1$ and $R^2$ taken together may form a ring;
$R^3$=H, $C_1$-$C_6$ alkyl, or phenyl;
or a pharmaceutically acceptable salt or N-oxide derivative thereof.

Also provided is a pharmaceutical composition for protecting against oxygen-derived free radical damage in a mammal, comprising a protective amount of a compound of the formula:

$$Z-NH-CO-NH(CH_2)_n-N\underset{(CH_2)_{n'}}{\overset{\overset{L}{\|}}{\diagup}}Y \quad (I)$$

where
L=O or S;
Y=O or NH;
Z=naphthyl, or phenyl or substituted phenyl, optionally substituted with 1 or 2 groups selected from:
$C_1$-$C_6$ alkyl, straight or branched, $C_3$p14 $C_6$ cycloalkyl, $NO_2$, $S(O)_pR^1$, halogen, $N(O)_{n'}R^1R^2$, $OR^3$, $Cf_3$, $$-N\diagdown\diagup NH \quad \text{or} \quad -N\diagdown\diagup O,$$

or Z=

$$\underset{S}{\diagup\!\!\diagdown}, \quad \underset{O}{\diagup\!\!\diagdown} \quad \text{or} \quad \underset{\underset{R^1}{N}}{\diagup\!\!\diagdown};$$

n'=0 or 1;
n=0, 2 or 3;
p=0–2;
$R^1$ and $R^2$ are, independently, H, $C_1$-$C_6$ alkyl, and $R^1$ and $R^2$ taken together may form a ring;
$R^3$=H, $C_1$-$C_6$ alkyl, or phenyl;
or a pharmaceutically acceptable salt or N-oxide derivative thereof; and a pharmaceutically acceptable carrier.

The invention relates further to a method for protecting against oxygen-derived free radical damage in a mammal, comprising administering to the mammal a protective amount of a compound of Formula I above, wherein Z is $$X_m-\!\!\diagdown\!\!\bigcirc\!\!\diagup\!\!-$$

where
X is F or $OCH_3$, and m is 0–2;
Y is O or NH;
L is O;
n is 0 or 2; and
n' is 0 or 1,
or a pharmaceutically acceptable salt thereof; Also provided is a pharmaceutical composition for protecting against oxygen derived free radical damage in a mammal, comprising a protective amount of such compound, and a pharmaceutically acceptable carrier.

Specifically preferred in the methods and pharmaceutical compositions of the invention are the following compounds, as well as pharmaceutically acceptable salts and N-oxide derivatives thereof:
(1) 1-[2-(2-oxo-1-imidazolidinyl)ethyl]-3-phenylurea (2) 1-[2-(2-oxo-1-imidazolidinyl)ethyl]-3-(4-fluorophenyl)urea (3) 1-[2-(2-oxo-1-imidazolidinyl)ethyl]-3-(4-dimethylaminophenyl)urea (4) 1-[2-(2-thio-1-imidazolidinyl)ethyl]-3-(4-dimethylaminophenyl)urea (5) 1-[2-(2-oxo-1-imidazolidinyl)ethyl]-3-(3-trifluoromethylphenyl)urea (6) 1-[2-(2-oxo-1-imidazolidinyl)ethyl]-3-(4-methoxyphenyl)urea (7) 1-[2-(2-oxo-1-imidazolidinyl)ethyl]-3-(3-trifluoromethyl-4-methoxyphenyl)urea (8) 1-[2-(2-oxo-1-imidazolidinyl)ethyl]-3-(3-trifluoromethyl-4-dimethylaminophenyl)urea.

DETAILED DESCRIPTION OF THE INVENTION

The compounds useful in this invention are described in and prepared by methods set forth in U.S. Pat. No. 4,032,638, the disclosure, synthesis and synthetic examples of which are hereby incorporated by reference.

The invention can further be understood by the following example in which parts and percentages are by weight unless otherwise indicated; all temperatures are in degrees centigrade.

EXAMPLE 1

1-2-(2-Oxo-1-imidazolidinvl)ethyl)-3-phenylurea [m=0, n=1, n'=0, Y=NH]

To a mixture of 6.5 g of commercially available 1-(2-aminoethyl)-2-imidazolidone and 50 ml benzene was added 5.5 ml of phenyl isocyanate. The strongly exothermic reaction was moderated by cooling to 25°. The mixture was stirred at 25° for 4 hr. It was cooled in ice and the mixture was filtered. The solid product was crystallized from 250 ml of acetone to give 6.8 g of white 1-[2-(2-oxo-1-imidazolidinyl)ethyl]-3-phenylurea, mp 162°-164°.

IR(Nujol)—3.1μ (NH): 5.9(C=O)

NMR(DMSO-d6)-m(1H) 8.45 δ (ArNH) m(5H) 6.7-7.5 (aromatic H): m(2H) 5.9-6.3 (NH); m(8H) 3.0-3.5 (CH$_2$).

A second crop, 1.5 g, mp 160°-163° brought the total yield to 8.3 g (67% yield). Increased yields were obtained when the starting imidazolidone (Aldrich technical grade) was purified by dissolving in chloroform, drying over magnesium sulfate, and distilling. To 19.5 g of this purified material in 150 ml of glyme was added 16.5 ml of phenyl isocyanate with ice cooling. The clear solution was, after 18 hr at 25°, concentrated at reduced pressure. Hexane was added to the solid residue and the mixture was filtered. The solid product was suspended in 500ml hot acetone, cooled and filtered to give 32.2 g of white solid, mp 168°-170° (86% yield).

Calcd. for $C_{12}H_{16}N_4O_2$; C 58.05; H 6.50: N 22.57. Found: C 58.07; H 6.72; N 21.94 58.21, 6.82 21.92.

Following the procedure of Example 1 or the synthetic procedures described in U.S. Pat. No. 4,032,638, the compounds in Table 1 can be prepared.

TABLE 1

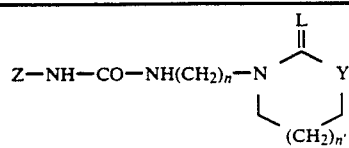

$$Z-NH-CO-NH(CH_2)_n-N\underset{(CH_2)_{n'}}{\overset{\overset{L}{\|}}{\diagup\diagdown}}Y$$

| Ex. | Z | n | n' | Y | L | m.p. (°C.) |
|---|---|---|---|---|---|---|
| 2 | 4-F-phenyl | 2 | 0 | NH | O | 177-178 |
| 3 | 4-OCH$_3$-phenyl | 2 | 0 | NH | O | 154-157 |
| 4 | 2-F-phenyl | 0 | 1 | O | O | 190-193 |
| 5 | 2,4-OCH$_3$-phenyl | 0 | 1 | O | O | 183-190 |
| 6 | phenyl | 0 | 0 | NH | O | 99-110 |
| 7 | 4-Cl-phenyl | 2 | 0 | NH | O | 132-135 |
| 8 | 2,4-Cl-phenyl | 2 | 0 | NH | O | 188-191 |
| 9 | 4-F-phenyl | 0 | 1 | O | O | 216-219 |
| 10 | 3-F-phenyl | 0 | 1 | O | O | 199-203 |
| 11 | phenyl | 2 | 0 | NH | S | 169-170 |
| 12 | phenyl | 0 | 1 | O | O | 204-207 |
| 13 | 4-(CH$_3$)$_2$N-phenyl | 2 | 0 | NH | O | |
| 14 | 4-(CH$_3$)$_2$N-phenyl | 2 | 0 | NH | S | |
| 15 | 3-CF$_3$-phenyl | 2 | 0 | NH | O | 150-154 |
| 16 | 3-CF$_3$-4-OCH$_3$-phenyl | 2 | 0 | NH | O | |
| 17 | 3-CF$_3$-4-(CH$_3$)$_2$N-phenyl | 2 | 0 | NH | O | |

UTILITY

Results of the various biological tests described below establish that the compounds of this invention have the property of inducing the antioxidant enzymes superoxide dismutase (SOD) and catalase (CAT) in mammalian cells and in organs of rats. These compounds were previously shown to protect plants against the deleterious effects of atmospheric ozone and their efficacy as plant protectants has been substantiated. [Carnahan, J. E., Jenner, E. L., Wat, E. K. W., Phytopathology 68, 1225-1229, (1978), Lee, E. H., Bennett, J.H., Plant Physiol. 69:1444-1449, (1982)]. However, these compounds have not previously been used in mammalian cells or in whole animals to induce anti-oxidant enzymes, nor to protect against oxygen-derived free radical tissue damage. Moreover, it was not predictable that they would have such activity in mammals.

Oxygen-derived free radicals have the potential to mediate cell injury in mammals. The first line of defense against such radicals is SOD which dismutes the superoxide anion radical ($O_2-$) to $H_2O_2$. Subsequent reactions may involve the antioxidant enzymes CAT and glutathione peroxidase (GSH-PX). Together, these three antioxidant enzymes help prevent cellular and tissue damage resulting from oxygen-derived free-radicals [Freeman, B.A., Crapo, J. D., Lab Invest. 47:412-425, (1982): Chow, C. K., Tappel, A. L., Lipids, 7:518-524 (1972); Fridovich, I., Arch. Biochem. Biophys. 247:1-11, (1986)]. Diseases that may be mediated by oxygen-derived free-radicals include adult respiratory distress syndrome, oxygen toxicity in premature infants, arthritis, organ transplant rejection, organ preservation, coronary occlusion and ischemic-reperfusion injures, radiation sickness and generalized shock.

Induction of endogenous SOD, CAT and/or GSH-PX activities ameliorates the effects of oxygen-derived free radicals in mammals. Such induction has been shown to be protective. For example, induction of these antioxidant enzymes results in increased tolerance to hyperoxia [Deneke, S. M. & Fanburg, B. L., N. Eng. J. Med. 303:76-86, (1980); Frank, L., Yam, J., Roberts, R. J., J. Clin. Invest. 61:269-275, (1978)]. Induction of these enzymes in response to hyperoxia protects against paraquat toxicity, since paraquat increases superoxide radical production. [Frank. L., *Biochem Pharmacol.,* 30:2319-2324, (1981)]. Known inducers of the anti-oxidant enzymes, such as $O_2$, $O_3$ and paraquat, are cytotoxic, but the compounds of this invention are not. Unlike $O_2$, $O_3$, and paraquat, the compounds of this invention do not generate oxygen-derived free-radicals in human neutrophils, nor do they act as scavengers of such radicals [Amoruso, M. A., Witz, G., Brennan, E. *The Toxicologist.* 7:148 (1987)]. Induction of SOD in mammalian cells that is not a specific response to the oxygen-derived superoxide anion radical has not been previously demonstrated.

These compounds are expected to have utility in the prevention and/or treatment of a variety of cardiovascular, inflammatory, and central nervous system diseases associated with oxygen-derived free radical damage. Such conditions include skin diseases, kidney and other organ transplants, ischemic and other reperfusion injury such as heart attack or stroke, acute or chronic lung inflammation, such as ARDS, emphysema, and oxygen injury in premature infants. Other potential utility may include protection from ionizing radiation and organ preservation.

METHODS

1. In vitro Administration of compounds of Examples 1 or 2 (Compound 1 and Compound 2, respectively).

Two different cell types, human gingival fibroblasts (Gin-1) and bovine aortic endothelial cells (CPA ATCl CCL207) were obtained from the American Type Culture Collection. They were incubated until confluent in Dulbecco's modified Eagles medium, supplemented with 2 mM glutamine and 10% heat-inactivated fetal calf serum at 37° C. in a humidified chamber with 5% $CO_2$ in air. Compounds were dissolved in DMSO, diluted to 100 mM with distilled deionized $H_2O$, and further diluted with Dulbecco's medium (without fetal bovine serum), to desired concentrations. The usual time of incubation with the compounds of this invention was 24 hr at 37° C. in a humidified incubator with 5% $CO_2$ in air. Lactic dehydrogenase (LDH) release was determined in several in vitro preparations as an index of cytotoxicity. using Sigma Diagnostic Kit #500. LDH release was expressed as a percentage of total LDH activity released from cells treated with 0.4% Triton X [Cabaud, P. G., Wroblewski, F. *Am. J. Clin. Pathol.* 30:234-236, (1958)].

Prior to the enzymatic assays the Gin-1 cells and aortic endothelial cells were prepared as follows: cells were rinsed several times with phosphate buffered saline without $Ca^{+2}$ or $Mg^{+2}$, removed from the culture flasks with 0.25% trypsin, counted using a hemocytometer, and resuspended at $2-3 \times 10^6$ cells/ml in Dulbecco's medium without fetal calf serum. Cells were then disrupted by pulse sonication and centrifuged at 100,000 xg at 4° C. Total protein [Bradford, M. M., *Anal. Biochem* 72:248-254, (1976)] and enzyme activities were determined on the cell sonicates, using standard techniques, SOD activity was determined using the method of McCord and Fridovich [McCord, J., Fridovich I., *J. Biol. Chem.* 244:6049-6055, (1969)]. Catalase activity was measured using the method of Beers and Sizer [Beers, R. F., Sizer, I. W., *J. Biol. Chem.* 195:133-146, (1952)]. Glutathione peroxidase activity was determined by the method of Guenzler et al. [Guenzler, W. A., Kremers, H., Flohe, L., *Z. Klin. Chem. Klin. Biochem.* 12:444-448 (1974)].

2. In Vivo Administration of Compound 1.

Male Lewis rats (250 g) were injected with 0.9% saline (controls) or Compound 1 (100 mg/kg) intraperitoneally twice a day for two days. Heart, liver and lungs were removed en bloc, dissected free of extraneous tissue, and blotted dry to remove contaminating blood. A portion of each tissue (approximately 0.5 g) was homogenized, and centrifuged at 500 xg for 10 minutes at 4° C. A 2 ml aliquot of supernatant was removed and centrifuged at 25,000 xg for 30 minutes. The supernatants were then decanted, and analyzed for SOD and CAT activities and total protein as described above.

All enzyme activities were expressed as units of activity per mg protein. The data were compared by Student's t test [Snedecor, W. G., *Statistical Methods,* p. 45, (1964)]. The level of significance was taken as $p<0.05$.

RESULTS

1. In vitro Induction of Antioxidant Enzymes by Heterocyclic Urea Compounds.

TABLE 1

Activities of Anti-Oxidant Enzymes with EDU in Gin-1 Cells

| Treatment Compound 1 | SOD U/mg Protein (n=7) | CAT U/mg Protein (n=4) | GSH-PX U/mg Protein (n=6) | LDH % |
|---|---|---|---|---|
| 0 mM | 7.7 ± 0.7 | 5.6 ± 0.9 | 44.0 ± 4.4 | 6 ± 1 |
| 0.125 mM | 13.1 ± 1.5* | 9.1 ± 1.1* | 52.1 ± 4.7 | 7 ± 2 |
| 0.25 mM | 20.7 ± 3.3* | 10.0 ± 1.8* | 45.8 ± 3.5 | not done |
| 1.0 mM | 11.6 ± 1.4* | 11.2 ± 2.0* | 45.1 ± 5.3 | 8 ± 2 |
| 2.0 mM | 13.5 ± 1.7* | 13.9 ± 1.6* | 47.8 ± 3.8 | not done |

Mean ± SEM *P < 0.05 Compared with 0 mM Controls

Both SOD and Cat activities significantly increased (P<0.05) in the presence of 0.125-2.0 mM Compound 1 compared with controls. GSH-PX activity remained constant. There was no indication of cytotoxicity, as shown by LOH release. Thus, surprisingly, Compound 1 induces anti-oxidant enzyme activities in mammalian cells in vitro.

TABLE 2

Activities of Anti-Oxidant Enzymes with EDU in Bovine Aortic Endothelial Cells

| Treatment Compound 1 | SOD U/mg Protein (n = 10) | CAT U/mg Protein (n = 6) | GSH-PX U/mg Protein (n = 6) |
|---|---|---|---|
| 0 mM | 4.2 ± 0.6 | 21.9 ± 2.2 | 28.4 ± 4.5 |
| 0.25 mM | 6.7 ± 0.8* | 25.7 ± 3.6 | 28.1 ± 5.7 |
| 0.05 mM | 9.5 ± 1.8* | 27.1 ± 3.3 | 33.5 ± 3.2 |
| 1.0 mM | 12.2 ± 3.4* | 31.9 ± 2.4* | 59.8 ± 17 |

Mean ± SEM *P < 0.05 compared with 0 mM Controls

SOD activity in bovine aortic endothelial cells treated with Compound 1 significantly increased (P<0.05) in a concentration-dependent manner. Catalase acitvity significantly increased at the highest concentration (1 mM) only, and GSH-PX was not significantly different. These results are similar to those from the Gin-1 cells: Compound 1 induces anti-oxidant enzyme activities in vitro in a second cell type.

TABLE 3

Activities of Anti-Oxidant Enzymes with Compound 2 in Gin-1 cells

| Treatment Compound 2 | Enzymes | | |
|---|---|---|---|
| | SOD U/mg Protein (n = 8) | CAT U/mg Protein (n = 6) | GSH-PX U/mg Protein (n = 6) |
| 0 mM | 8.6 ± 0.8 | 6.9 ± 0.6 | 36.0 ± 3.2 |
| 0.25 mM | 15.2 ± 1.6* | 8.3 ± 0.8 | 35.0 ± 1.4 |
| 0.50 mM | 15.9 ± 1.7* | 11.4 ± 1.8* | 40.0 ± 4.7 |
| 1.0 mM | 14.5 ± 2.2* | 9.5 ± 1.4 | 39.1 ± 4 |

Mean ± SEM *P < 0.05 compared with 0 mM Controls

Compound 2 demonstrated similar effects to Compound 1 in Gin-1 cells. SOD and CAT activities were significantly increased (P<0.05) at one or more concentrations, while GSH-PX activity remained constant. The efficacy of the two compounds was similar.

2. In vivo Industion of Antioxidant Enzyme SOD by the Heterocyclic Urea Compound 1.

TABLE 4

SOD Activity in Rat Heart, Liver and Lung After Treatment with Compound 1

| Treatment | Tissue SOD Activity (U/mg Protein) | | |
|---|---|---|---|
| | Heart (8) | Liver (8) | Lung (8) |
| Saline Control (0.9%) | 157 ± 8 | 278 ± 37 | 99 ± 12 |
| Compound 1 (100 mg/kg) | 194 ± 14* | 444 ± 68* | 134 ± 7* |

Mean ± SEM *P < 0.05 compared with Saline Control. EDU injected intraperitoneally 2 × /day for 2 days.

Compound 1 induced SOD activity in all three tissues studied compared with controls Thus, surprisingly, Compound 1 has shown in vivo activity in mammals in addition to in vitro activity. Recently, additional in vivo activity has been reported. Treatment with Compound 1 decreased polymorphonuclear leukocyte infiltration into ozone-exposed rat lungs [Bassett, D. J. P., Elbon, C. L., Reichenbaugh, S. S., Adler, R., Boswell, G. A., Stevens, T. M., Kerr, J. S., Am. Rev. Resoir. Dis. 137:145, (1988)]. The data indicate Compound 1 shows efficacy in an in vivo model involving the production of oxygen-derived free radicals and lipid peroxidation products. The compounds would therefore be expected to reduce acute toxicity to the lung involving polymorphonuclear leukocytes, including ARDS (adult repiratory distress syndrome).

The compounds of Examples 7, 11, and 12 (see Table 1) were also tested in the in vitro human gingival fibroblast assay (Gin-1) in the manner described above. The activities of antioxidant enzymes after treatment with these compounds were as follows:

TABLE 5

Activities of Antioxidant Enzymes in Gin-1 Cells

| Treatment Ex. # | SOD U/mg Protein (#) | % Increase | CAT U/mg Protein (#) | % Increase |
|---|---|---|---|---|
| — | 3.8 ± 1.5 (4) | — | 1.9 ± 0.9 (4) | — |
| 7 | 5.8 ± 1.2 (8) | 51 | 3.6 ± 0.9 (4) | 95 |
| 11 | 4.0 ± 0.8 (8) | 3 | 4.1 ± 1.6 (4) | 118 |
| 12 | 6.5 ± 0.9 (4) | 69 | 2.5 ± 0.6 (4) | 35 |

Number in parentheses is the number of experiments. All compounds were incubated with Gin-1 cells at a concentration of 1.0 mM for 24 hours.

Either SOD or CAT, or both enzymes, increased in the presence of the compounds of Examples 7, 11, and 12. Compound Ex. 11 had the least effect on SOD activity, but affected CAT the most. In contrast, compound Ex. 12 had the greatest effect on SOD and the least effect on CAT. Thus, these three compounds induce antioxidant enzyme activities in mammalian cells in vitro and would be expected to provide protection against oxygen-derived free radical damage in mammals in vivo.

DOSAGE FORMS

The compounds (active ingredients) of this invention can be administered to reduce or protect against oxygen-derived free radical injury by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a amount of active ingredient sufficient to reduce or protect against oxygen derived free radical injury and will, of course, vary depending upon known factors such as the pharmacodynamic characteristics of the particular active ingredient, and its mode and route of administration: age, health, and weight of the recipient nature and extent of symptoms or free-radical exposure: kind of concurrent treatment, frequency of treatment, and the effect desired. Usually a daily dosage of active ingredient can be about 0.1 to 400 milligrams per kilogram of body weight. Ordinarily 1 to 100, and preferably 10 to 50 milligrams per kilogram per day is effective to obtain desired results.

Dosage forms (compositions) suitable for internal administration contain from about 10–500 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Reference to the compounds of this invention includes pharmaceutically acceptable acid addition salts and N-oxide derivatives thereof. By the term "pharmaceutically acceptable acid addition salt" is meant any non-toxic pharmaceutically suitable salt of a compound described above which has the desired pharmacological properties in mammals. Preparation of such salts is well known to those skilled in the pharmaceutical sciences. Pharmaceutically acceptable acid addition salts of the above compounds include the hydrochloride, hydrobromide, hydroiodide, sulfate, bisulfate, nitrate, citrate, tartrate, bitartrate, lactate, phosphate, malate, maleate, fumarate, succinate, acetate, and pamoate. Methods for preparation of N-oxide derivatives are also well known in the art.

CAPSULES

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

We claim:

1. A method of protecting against oxygen-derived free medical damage in a mammal by inducing the endogenous antioxidant enzymes superoxide dismutase or catalase, comprising administering to the mammal a protective amount of a compound of the formula:

$$Z-NH-CO-NH(CH_2)_n-N \underset{(CH_2)_{n'}}{\overset{L}{\underset{\|}{\diagup}}} Y$$

where
L = O or S;
Y = O or NH;
Z = naphthyl, or phenyl or substituted phenyl, optionally substituted with 1 or 2 groups selected from:
$C_1-C_6$ alkyl, straight or branched, $C_3-C_6$ cycloalkyl, $NO_2$, $S(O)_p R1$, halogen, $N(O)_{n'}R^1R^2$, $OR^3$, $CF_3$, $-N\overbrace{\phantom{xxx}}NH$ or $-N\overbrace{\phantom{xxx}}O$, or Z =

$\underset{S}{\diagdown\!\diagup}$ , $\underset{O}{\diagdown\!\diagup}$ or $\underset{\underset{R^1}{|}}{\underset{N}{\diagdown\!\diagup}}$ ;

n' = 0 or 1;
n = 0, 2 or 3;
p = 0-2;
$R^1$ and $R^2$ are, independently, H, $C_1-C_6$ alkyl, and $R^1$ and $R^2$, taken together, may form a ring;
$R^3$ = H, $C_1-C_6$ alkyl, or phenyl;
or a pharmaceutically acceptable salt or N-oxide derivative thereof.

2. A method of claim 1, wherein $$Z \text{ is } X_m-\!\!\langle\bigcirc\rangle\!\!-$$

where
X is F or $OCH_3$, and m is 0–2;
Y is O or NH;
L is O;
n is 0 or 2; and n' is 0 or 1.

3. A method claim 1, which comprises administering 1-[2-(2-oxo-1-imidazolidinyl)ethyl]-3-phenylurea.

4. A method of claim 1, which comprises administering 1-[2-(2-oxo-1-imidazolidinyl)ethyl]-3-(4-fluorophenyl)urea.

5. A method of claim 1, which comprises administering 1-[2-(2-oxo-1-imidazolidinyl)ethyl]-3-(4-dimethylaminophenyl)urea.

6. A method of claim 1, which comprises administering 1-[2-(2-thio-1-imidazolidinyl)ethyl]-3-(4-dimethylaminophenyl)urea.

7. A method of claim 1, which comprises administering 1-[2-(2-oxo-1-imidazolidinyl)ethyl]-3-(3-trifluoromethylphenyl)urea.

8. A method of claim 1, which comprises administering 1-[2-(2-oxo-1-imidazolidinyl)ethyl]-3-(4-methoxyphenyl)urea.

9. A method of claim 1, which comprises administering 1-[2-(2-oxo-1-imidazolidinyl)ethyl]-3-(3-trifluoromethyl-4-methoxyphenyl)urea.

10. A method of claim 1, which comprises administering 1-[2-(2-oxo-1-imidazolidinyl)ethyl]-3-(3-trifluoromethyl-4-dimethylaminophenyl)urea.

* * * * *